US006759658B2

United States Patent
Overdick et al.

(10) Patent No.: US 6,759,658 B2
(45) Date of Patent: Jul. 6, 2004

(54) X-RAY DETECTOR HAVING A LARGE DYNAMIC RANGE

(75) Inventors: Michael Overdick, Langerwehe (DE); Walter Ruetten, Linnich/Ederen (DE); Thomas Zaengel, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 204 days.

(21) Appl. No.: 10/067,427

(22) Filed: Feb. 5, 2002

(65) Prior Publication Data

US 2002/0109091 A1 Aug. 15, 2002

(30) Foreign Application Priority Data

Feb. 10, 2001 (DE) ......................................... 101 06 221

(51) Int. Cl.[7] .............................................. G01T 1/00
(52) U.S. Cl. ............................... 250/336.1; 250/370.11
(58) Field of Search ........................ 250/336.1, 370.11, 250/370.14, 363.07, 363.02; 25/370.11; 364/414

(56) References Cited

U.S. PATENT DOCUMENTS

| | | | | |
|---|---|---|---|---|
| 3,646,347 A | * | 2/1972 | Farmer et al. | 250/369 |
| 4,087,692 A | * | 5/1978 | Lecuyer et al. | 250/370.07 |
| 4,528,450 A | * | 7/1985 | Valenta | 250/362 |
| 4,591,984 A | | 5/1986 | Mori | 364/414 |
| 6,498,335 B2 | * | 12/2002 | Modlin et al. | 250/214 SW |
| 2003/0053587 A1 | * | 3/2003 | Demharter | 378/19 |

FOREIGN PATENT DOCUMENTS

| EP | 0434154 | 3/1995 | ......... H01L/27/146 |
|---|---|---|---|
| EP | 0440282 | 4/1996 | ............ H04N/3/15 |

OTHER PUBLICATIONS

"A counting pixel readout chip for imaging applications", P. Fischer et al., Nucl. Instr. and Meth. A 405 (1998), pp. 53–59.

* cited by examiner

*Primary Examiner*—David Porta
*Assistant Examiner*—Christine Sung

(57) ABSTRACT

The invention relates to an X-ray detector which includes at least one conversion unit (1) for converting absorbed X-ray quanta into electric charge signals, at least one evaluation unit (10) for amplifying and further processing the charge signals, and at least one data processing unit (11) for the acquisition, further processing and output of data. The charge signals are first amplified by an input amplifier (2) in the evaluation unit (10) after which they are evaluated in parallel in a counting channel (5) as well as in an integrator channel (7). The charge signals are then counted in the counting channel and the overall charge is integrated in the integrator channel as a measure of the energy delivered in the conversion unit (1). Because of the parallel presentation of the counting results and the integration results, more weight can be attached thereto in their respective range of the quantum flow that is optimum from a measuring point of view, so that the dynamic range of the X-ray detector is enlarged. Furthermore, additional information, for example, the mean absorption energy of the X-ray quanta, can be determined from the combination of the signals.

9 Claims, 1 Drawing Sheet

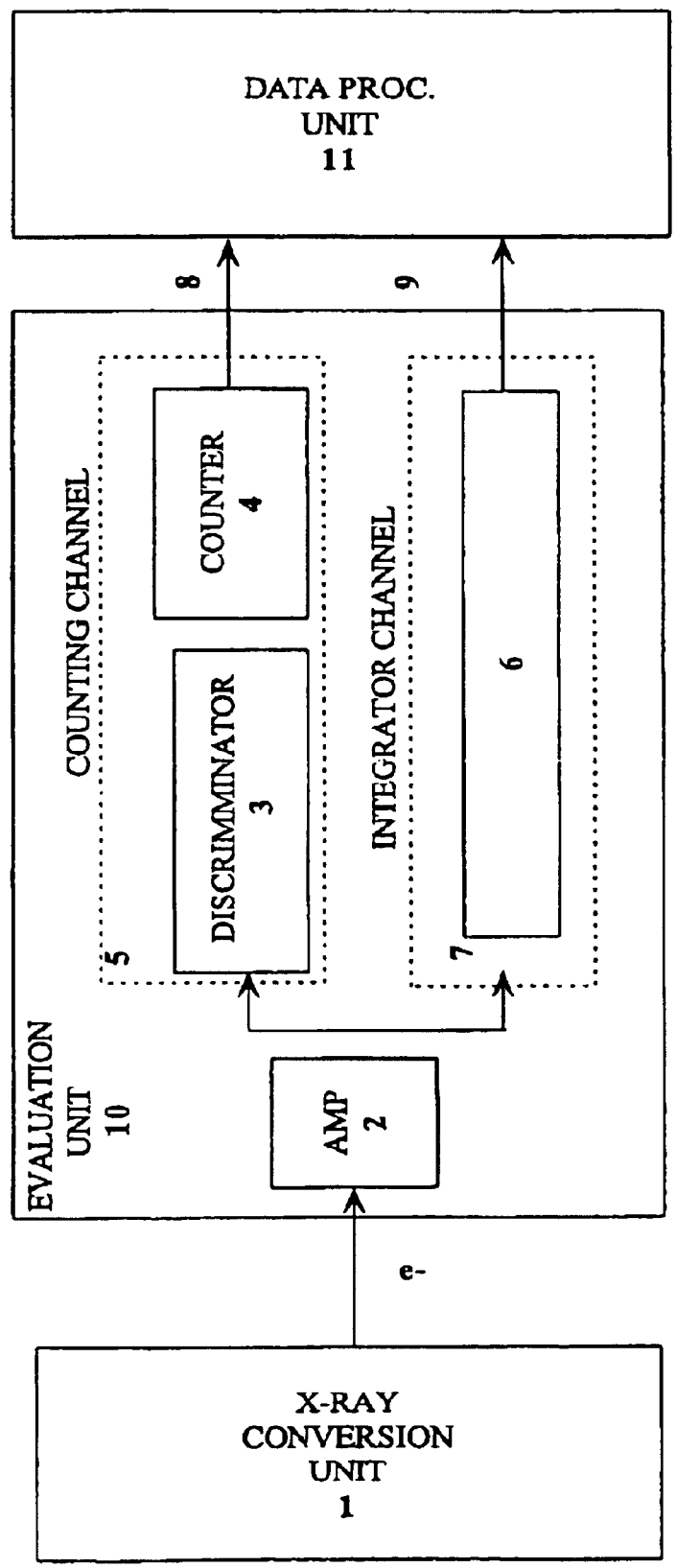

X-RAY DETECTOR HAVING A LARGE DYNAMIC RANGE

The invention relates to an X-ray detector which includes at least one conversion unit, at least one evaluation unit for the counting and integration of absorbed X-ray quanta, and also at least one data processing unit. The invention also relates to a method of evaluating the absorption signals of an X-ray detector which is preferably arranged so as to face an X-ray source in a computed tomography apparatus, and to an X-ray examination apparatus which includes an X-ray source for the emission of X-rays and an X-ray detector.

Absorbed X-ray quanta are converted into electric charge signals in X-ray detectors and X-ray imaging systems. X-ray detectors of this kind are used, for example, in computed tomography (CT) in the medical field. Further applications of X-ray detectors can be found in the industrial field (for example, for the testing of materials) or in the field of security. Normally speaking, (dynamic) X-ray detectors then consist of:

a) a conversion unit or stage which absorbs a large part of the incident X-ray quanta so as to convert such quanta into electric charge signals,
b) an evaluation unit or stage in which the signals from the conversion unit are amplified and further processed, as well as
c) a data processing unit or stage which includes means for data acquisition, for control and for output of the acquired signals.

Two different processing concepts are customarily utilized in the evaluation unit. For example, on the one hand there are integrating evaluation units of the kind disclosed, for example, in EP 434 154 or EP 440 282. The charge signals which are prepared by these conversion units are integrated over a predetermined period of time, that is, the so-termed integration period. In the ideal case the result of this integration represents the energy deposited by the absorbed X-ray quanta during the integration period in the conversion unit.

There is also the concept of counting evaluation units (see P. Fischer et al., "A counting pixel readout chip for imaging applications", Nucl. Instr. and Meth. A 405 (1998), pp. 53 to 59). Therein, the charge pulses produced by individual X-ray quanta in the conversion unit are individually acquired and counted. To this end, use is customarily made of a signal-forming amplifier which is succeeded by a comparator whose digital output signals are counted by a counter. In the ideal case the number of the charge pulses counted within a counting period thus corresponds exactly to the number of X-ray quanta absorbed in the conversion unit during this time. The advantage of the counting method resides in the fact that a very large counting range having in principle an ideal linearity can thus be covered. The counting range in principle is limited only by the depth of the counter used. This method, however, imposes a problem in that the count rates (that is, the number of counting pulses per unit of time) that can be reached are limited due to various idle time effects, in which no signals can be detected, and also by a limited bandwidth of the analog electronic circuitry.

In contrast therewith, the integration method also enables operation in the case of very high quantum flows. However, this method is rather limited in respect of usable dynamic range and linearity. For the integration method it is also known that, because of various afterimage effects, residues of preceding X-ray images may still be present in subsequent images. An example in this respect is the afterglow that is known to occur in many scintillators. Generally speaking, counting detectors are less susceptible to such afterimage effects, because the afterimage effects normally do not give rise to significant short-time charge pulses and hence do not falsify the counting results.

Furthermore, U.S. Pat. No. 4,591,984 discloses an X-ray detector in which the charge signals from a conversion unit can be subjected alternatively to counting or to integration. For counting the pulses are applied to a pulse height analyzer whose output is activated only when the charge signal exceeds a threshold value. The frequency of activation of the output can then be counted by a counter. Alternatively, however, the charge signals can also be applied to a low-pass filter in an integration circuit, the charges then being accumulated over a selectable period of time in a capacitor. When the integration result is to be evaluated, the capacitor is discharged with a constant current. For as long as the voltage of the capacitor remains higher than a reference voltage, the pulses of an external clock signal are applied to the previously mentioned counter in which they are counted. The larger the charge accumulated in the capacitor, the longer the discharge operation will last and the longer the voltage of the capacitor will remain higher than the reference voltage. As a result, a correspondingly larger number of pulses of the clock signal will be counted by the counter.

Either the output pulses of the pulse height analyzer or the conducted pulses of the external clock signal can be applied to the counter by switching over a switch in the X-ray detector which is known from U.S. Pat. No. 4,591,984. Depending on the position of the switch, therefore, the absorbed X-ray quanta are counted or the absorbed radiation energy is measured. Because the counting method is more exact in the case of small quanta flows while the integration method is more exact for higher quanta flows, the relevant better measuring method can be applied each time by choosing the appropriate switch position. The user then has to guess in advance which quanta flows are to be expected, so that the user can choose the appropriate switch position. However, this is a drawback since advance knowledge about the best method to be used is necessary. When the switch is set to the wrong position, the result of an X-ray operation cannot be evaluated by means of the optimum method. In given circumstances it may then be necessary to repeat the X-ray operation; this should be avoided at all costs in particular in the case of medical applications, because the patient is then exposed to an additional radiation load.

Considering the foregoing it is an object of the present invention to provide an improved X-ray detector, a method of evaluating the signals of an X-ray detector and an X-ray examination apparatus with an X-ray detector which enable optimum measurement in a wide dynamic range without necessitating presetting by a user.

This object is achieved by means of an X-ray detector as disclosed in the characterizing part of claim 1 as well as by means of a method as disclosed in the characterizing part of claim 8. Advantageous further embodiments are disclosed in the dependent claims.

The X-ray detector in accordance with the invention includes the following elements:

a) at least one conversion unit in which X-ray quanta are absorbed so as to generate an electric charge signal whose magnitude corresponds to the absorbed energy,
b) at least one evaluation unit in which said charge signal from the conversion unit is processed in parallel in a counting channel and in an integrator channel, the counting output of the counting channel presenting a measure of the number of charge signals detected since the beginning of measurement, and the integrator output of the integrator channel presenting a measure of the overall charge detected since the beginning of measurement, which beginning of measurement for the counting channel is preferably being identical to the beginning of measurement for the integrator channel, be it that this is not absolutely necessary, c) at least one data processing unit that processes the signals from the counter output and from the integrator output in combination so as to determine the absorbed quantity of X-rays.

The evaluation unit in the X-ray detector thus performs a counting method and an integration method in parallel for the charge signals generated; the results of these methods are used together in the data processing unit so as to determine an overall result for the absorbed quantity of X-rays. The absorbed "quantity of X-rays" may then be the energy absorbed per unit of time as well as the number of X-ray quanta absorbed per unit of time; it may also be quantified as a suitably defined combined variable. The simultaneous execution of two measuring methods (counting and integration) offers the advantage that the user need not specify in advance which method alone is to be carried out, so that sub-optimum evaluation of the measuring results cannot happen by mistake. The X-ray detector in accordance with the invention thus operates in a significantly enlarged dynamic range in comparison with known detectors. This is important notably for medical applications, where the X-ray load is to be minimized, as well as for applications where estimation of the quanta flows to be expected either is not possible or very intricate.

The data processing unit in a preferred embodiment of the X-ray detector is arranged in such a manner that in the case of a low absorption rate of the X-ray quanta it attaches more weight to the signals from the counter output than to the signals from the integrator output. In the extreme case the weighting can be shifted to such an extent that the quantity of X-rays is determined exclusively on the basis of the signals from the counter output. In the case of low absorption rates or small quanta flows, the effect of the counting method is optimum, because idle time effects and small bandwidths are of no importance in that case. Electronic noise, dark currents and afterimage effects are strongly suppressed by the detection of individual charge signals. In contrast therewith, in the case of small quanta flows the integration method is comparatively inaccurate because of the electronic noise, dark currents and possible afterimage effects. The proposed stronger weighting of the counting method in the case of low absorption rates takes into account this typical aspect of the measuring method and hence gives rise to better final results because the more exact counting method is applied.

Furthermore, the data processing unit may be arranged in such a manner that in the case of a high absorption rate of the X-ray quanta it attaches more weight to the signals from the integrator output than to the signals from the counter output. In the extreme case the absorbed quantity of X-rays can then be determined exclusively from the signals from the integrator output. In the case of high absorption rates or high quantum flows the operation of the integrator channel is optimum, because electronic noise, dark currents and afterimage effects are practically of no importance. In contrast therewith, the accuracy of the counting channel is strongly influenced by idle time effects. The data processing unit thus again takes into account the characteristic behavior of the two measuring channels for the determination of the overall result, that is, in such a manner that they are weighted in conformity with their precision. Overall this yields a final result for the quantity of absorbed X-rays that is more exact than when only a single counting method is used.

The data processing unit in a further embodiment of the invention is arranged in such a manner that it determines the mean energy of the absorbed X-ray quanta from the signals from the counter output and the signals from the integrator output. Typically for this purpose the absorbed X-ray quanta are counted in a measuring interval and the energies then absorbed are integrated. At the end of the measuring interval the total absorbed energy is then divided by the number of absorbed X-ray quanta so as to obtain the mean energy per X-ray quantum. Such a mean energy deposited by the X-ray quanta contains valuable information that could not be recovered by means of one measuring method alone (counting or integration).

The evaluation unit is preferably constructed in such a way that it includes an input amplifier that preprocesses the charge signal presented by the conversion unit. The preprocessing may notably be a corresponding amplification of this signal. Furthermore, the charge signal may be converted into a different type of signal, for example, a voltage signal, which is more suitable for distribution to a plurality of channels. The preprocessed signal is applied from the input amplifier to the counting channel as well as to the integrator channel. Thus, in this configuration a single input amplifier is advantageously used to prepare the signals for the counting channel as well as for the integrator channel. This avoids the necessity of intricate control of the distribution among two channels of the quantities of charge which are prepared by the conversion unit and are usually small. The common use of an input amplifier, moreover, reduces the amount of structural means required and at the same time ensures that no artefacts are introduced by differences in the input amplification for the measuring channels.

The X-ray detector may be a single image element with only one conversion unit, one evaluation unit and one data processing unit. The X-ray detector, however, preferably includes a plurality of conversion units that are arranged so as to be distributed in one plane. This arrangement may notably be a matrix in which the plurality of conversion units is arranged in columns and rows and each conversion unit constitutes an image element (pixel) of an X-ray detector system.

Each conversion unit in such an X-ray detector arrangement comprising a plurality of conversion units is preferably associated with exactly one evaluation unit and exactly one data processing unit, so that the charge signals generated by the pixel in the form of the conversion unit can be quickly and reliably evaluated. Furthermore, all evaluation units and data processing units are advantageously constructed as microelectronic units on a common substrate which are electrically connected to the conversion units. The conversion units may then be arranged, for example above the electronic units on the substrate. In particular a CMOS technique can be used for the manufacture of the microelectronic structures.

The invention also relates to a method of evaluating the absorption signals of an X-ray detector which is preferably arranged so as to face an X-ray source in a computed tomography apparatus. The X-ray detector typically determines how large a quantity of X-rays is absorbed by an object to be examined which is arranged between the X-ray source and the detector, for example, the body of a patient. The method includes the following steps:

a) counting the X-ray quanta absorbed by the X-ray detector in a time interval;
b) integrating the absorption energies of the X-ray quanta absorbed in said time interval in order to determine the overall energy deposited in the X-ray detector,
c) determining the mean absorption energy of the X-ray quanta absorbed in said time interval from the measurements in the steps a) and b),
d) comparing the mean absorption energy from the step c) with the original emission spectrum of the X-ray source.

As opposed to conventional methods, in the novel method the number of absorbed X-ray quanta as well as the total energy deposited by this number is determined at the output side of the X-ray detector. The mean absorption energy per X-ray quantum can then be calculated from these two values as the quotient of the integral of the absorption energies and the number of X-ray quanta. Valuable information as regards the absorption behavior of the object examined, being dependent on the wavelength, can be derived by comparison of said mean absorption energy with the emission spectrum of the X-ray source that is considered to be known. For example, the absorption of X-ray quanta of low energy by the body tissue of a patient is higher than that of X-ray quanta of higher energy. Such a stronger absorption of low energy X-ray quanta becomes manifest as an increase of the mean X-ray quantum energy after passage through the body of the patient; this is referred to as "radiation hardening". Such radiation hardening varies in dependence on the type of irradiated tissue, so that it provides additional information as regards the relevant tissue. In an extreme case it is feasible for two irradiated objects to absorb each time the same percentage of the total energy applied and/or the same percentage of the number of applied X-ray quanta and hence cannot be distinguished strictly by determination of the absorbed energy or of the absorbed number of X-ray quanta. However, when these two objects absorb the X-ray quanta to a different degree at different wavelengths, they give rise to a different radiation hardening that can be detected by means of the method in accordance with the invention. The proposed combination of a counting method and an integration method thus enables the extraction of information that will not become available when the methods are used separately.

When the duration of the time interval for carrying out the counting and the integration in the method in accordance with the invention is chosen so as to be short enough, it is possible in theory to determine the energy of each individual absorbed X-ray quantum; the energy spectrum of the X-rays after their passage through the object to be examined can then be determined therefrom. In other words, the length of the time interval can influence the resolution with which the energy spectrum of the X-rays is determined after their passage through the object to be examined.

An X-ray detector of the kind set forth in which an evaluation unit processes charge signals from a conversion unit in parallel by way of a counting channel and an integrator channel is particularly suitable for carrying out the method.

The invention will be described in detail, by way of example, with reference to the accompanying FIGURE. The sole FIGURE shows a block diagram with the components of an X-ray detector in accordance with the invention.

The majority of the X-ray quanta is absorbed in the conversion unit 1 so as to be converted, after absorption, into an electric charge signal whose magnitude is approximately proportional to the absorbed energy. In the present context it is not important whether the conversion of the X-ray quanta into the charge signals takes place directly (by means of so-termed directly converting materials, for example, gases such as Xe, semiconductors such as GaAs, CdTe, CdZnTe, or photoconductors such as Se, $PbI_2$ or PbO) or indirectly (for example, by conversion into low energy light quanta by means of a scintillating material and subsequent detection by a photodiode of crystalline or amorphous silicon).

The charge signals generated by the conversion unit 1 are applied to the input amplifier 2 of the evaluation unit 10. The evaluation unit is realized typically as an integrated circuit, for example, as a CMOS circuit. The input amplifier 2 in the evaluation unit converts the charge signals into a different signal (for example, a voltage signal). The input amplifier is usually a charge sensitive amplifier (CSA), that is, typically an integrated circuit which often includes a bleeding resistor. For each brief charge pulse at the input such an amplifier produces an exponentially decreasing voltage at the output, the surface area below this exponential curve being proportional to the charge within the pulse.

A counting channel 5 and an integrator channel 7 are connected in parallel to the output side of the input amplifier 2. The counting channel consists of an event discriminator 3 which is succeeded by a counter 4. The event discriminator 3 typically consists of a signal shaping amplifier and a comparator with an adjustable threshold value. The event discriminator 3 serves to generate a digital output signal (counting pulse) for each charge pulse from the conversion unit 1 which is larger than a predetermined quantity of charge (see FIG. 1 in the publication by M. Overdick et al., "A "Bioscope" system using double-sided silicon strip detectors and self-triggering read-out chips", Nucl. Instr. and Meth. A 392 (1997), pp. 173 to 177). The counter 4 is an electronic digital counter with a counting depth of n bits. Linearly fed back shift registers (see the previously cited P. Fischer et al.) constitute a version that offers a particularly large saving of space.

The integrator channel consists of a circuit which may be referred to as an "overall signal acquisition circuit" 6 which detects the total quantity of charge delivered by the conversion unit 1 during an integration period. Inter alia the following possibilities exist so as to realize this circuit:

an integrator circuit with an analog output;
a voltage/frequency converter with subsequent counter (see DE 199 45 757.3);
a delta-sigma converter (see S. R. Norsworthy, R. Schreier, G. C. Temes, "Delta-Sigma Data Converters", IEEE Press, 1997).

The count of the counter 4 is applied from the counter output 8 to the data processing unit 11. Similarly, the result of the integration on the integrator output 9 is applied to the data processing unit. The data processing unit 11 can thus evaluate the results of the counting channel 5 as well as those of the integrator channel 7 in parallel. This results in an enlarged dynamic range of the X-ray detector in comparison with the present state of the art, because the more exact results of the counting channel can be used in the case of small quantum flows whereas in the case of large quantum flows the integrator channel that is more exact for large flows can be utilized. Therefore, the advantages of the two measuring methods can be combined by the counting as well as integrating acquisition of the signals in each pixel cell of an X-ray detector.

Moreover, in the case of average quantum flows it is possible to acquire additional information which is not available in the case of separate application of a counting method or an integration method. Because the integrator channel 7 detects the absorbed energy and the counting channel 5 determines the number of X-ray quanta absorbed, combination of the two signals enables, for example, determination of the mean energy of the absorbed quanta. This mean energy is a measure of the radiation hardening occurring in the object being examined; such information can be advantageously used for the determination and discrimination of types of tissue.

What is claimed is:

1. An x-ray detector which includes;
   (a) at least one conversion unit for the absorption of x-ray quanta while generating an electric charge signal which corresponds to the absorbed energy,
   (b) at least one evaluation unit which has a pair of parallel channels for concurrently processing said charge signals, the parallel channels including:
       a counter channel which count a number of charge signals detected since a beginning of a measurement interval, and,
       an integrator channel which measures overall charge of the charge signals detected since the beginning of the measurement interval;
   (c) at least one data processing unit which determines an absorbed quantity of x-rays from a combination of both the count of the number of charge signals from the counter channel and the overall charge measurement from the integrator channel.

2. The x-ray detector as claimed in claim 1, wherein the data processing unit is arranged in such a manner that it attaches more weight to the signals from the counter channel than to the signals from the integrator channel for a low absorption rate of the x-ray quanta.

3. The An x-ray detector as claimed in claim 1, wherein the data processing unit is arranged in such a manner that it determines a mean energy of the detected x-ray quanta from the signals from the counter channel and the signals from the integrator channel.

4. The x-ray detector as claimed in claim 1, wherein the evaluation unit includes an input amplifier which amplifies the charge signal presented by the conversion unit and conducts the amplified signal to the counting channel and to the integrator channel.

5. The x-ray detector as claimed in claim 1, further including:
   a plurality of conversion units which are distributed in one plane in the form of a matrix.

6. The x-ray detector as claimed in claim 5, wherein each conversion unit is associated with an evaluation unit and a data processing unit, all evaluation units and data processing units being formed as microelectronic units on a common substrate.

7. An x-ray detector comprising:
   (a) at least one conversion unit for the absorption of x-ray quanta while generating an electric charge signal which corresponds to the absorbed energy;
   (b) at least one evaluation unit for processing said charge signal in a counting channel whose counter output presents a measure of a number of the charge signals detected since a beginning of measurement as well as, in parallel therewith, in an integrator channel whose integrator output presents a measure of an overall charge of the charge signals detected since a beginning of measurement;
   (c) at least one data processing unit which processes the signals from the counter output and from the integrator output in combination so as to determine the absorbed quantity of x-rays, the data processing unit being arranged in such a manner that:
       it attaches more weight to the signals from the integrator output than to the signals from the counter output in the case of a high absorption rate of the x-ray quanta, and
       it attaches more weight to the signals from the counter output than to the signals from the integrator output in the case of a low absorption rate of the x-ray quanta.

8. A method of evaluating the absorption signals of an x-ray detector which is preferably arranged so as to face an x-ray source in a computed tomography apparatus, which method includes the following steps:
   (a) counting the x-ray quanta absorbed by the x-ray detector in a time interval;
   (b) integrating the absorption energies of the x-ray quanta absorbed in said time interval;
   (c) determining the mean absorption energy of the x-ray quanta absorbed in said time interval from the measurements in steps (a) and (b);
   (d) comparing the mean absorption energy from step (c) with the original emission spectrum of the x-ray source.

9. An x-ray examination apparatus which includes an x-ray source for the emission of x-rays with an original x-ray spectrum and an x-ray detector, the x-ray detector including:
   (a) at least one conversion unit for the absorption of x-ray quanta while generating an electric charge signal which corresponds to the absorbed energy;
   (b) at least one evaluation unit for processing said charge signal in parallel in:
       a counting channel whose counter output represents a measure of the number of charge signals detected in a measurement time interval,
       an integrator channel whose integrator output represents an integration of the absorbed energy of the x-ray quanta detected in the measurement time interval,
   (c) at least one data processing unit which:
       processes the signals from the counter output and from the integrator output in combination to determine the mean absorbed energy of the x-ray quanta absorbed in the measurement time interval, and
       comparing the mean absorbed energy in the measurement time interval with the original spectrum of the x-ray source.

* * * * *